United States Patent [19]
Schmidt et al.

[11] Patent Number: 6,103,482
[45] Date of Patent: Aug. 15, 2000

[54] EVALUATING THE SENSITIZING/IRRITANT/ALLERGENIC POTENTIAL OF A GIVEN SUBSTRATE

[75] Inventors: Rainer Schmidt, Clamart; Marcelle Regnier, Paris, both of France

[73] Assignee: Societe L'Oreal S.A., Paris, France

[21] Appl. No.: 09/022,276

[22] Filed: Feb. 11, 1998

[30] Foreign Application Priority Data

Feb. 11, 1997 [FR] France ................................. 97-01576

[51] Int. Cl.$^7$ ........................ G01N 33/567; G01N 33/53; C12Q 1/68
[52] U.S. Cl. ........................ 435/7.21; 435/7.24; 435/373; 435/6
[58] Field of Search ................................. 435/7.21, 7.24, 435/373

[56] References Cited

FOREIGN PATENT DOCUMENTS 0497399 8/1992 European Pat. Off. .
90/02796 3/1990 WIPO .

OTHER PUBLICATIONS

A. Rambukkana et al. "Effects of contact allergens on human Langerhans cells . . . "; Laboratory Investigation, vol. 74, No. 2, 1996, Washington, D.C., pp. 422–436, XP002043544.

F.H.M. Pistoor et al, "Novel predictive assay for contact allergens . . . ", American Journal of Pathology, vol. 149, No. 1, Jul. 1, 1996, Washington, D. C., pp. 337–343, XP002043821.

Muller, G., et al. Human keratinocyte–derived IL–12 affects LC–induced allogeneic T–cell responses. Advances in Experimental Medicine and Biology, 378:519–521, 1995.

Tsuchida, T., et al. Epidermal Langerhans cells can function as stimulatory cells but not as accessory cells in CTL induction. J. Immunol. 132:1163–1168, Mar. 1984.

Schuler, G., et al. Murine epidermal Langerhans cells mature into potent immunostimulatory dendritic cells in vitro. J. Exp. Med. 161:526–546, Mar. 1985.

Reid, C.D., et al. Interactions of tumor necrosis factor with granulocyte–macrophage colony–stimulating factor and other cytokines in the regulation of dendritic cell growth in vitro from early bipotent CD34+progenitors in human bone marrow. J. Immunol, Oct. 1992.

Roitt, I.M. and Delves, P.J. Editors. Encyclopedia of Immunology. Academic Press, London, p. 640, 1993.

Shimada, S., et al. Enhanced antigen–presenting capacity of cultured Langerhans cells is associated with markedly increased expression of la antigen. J. Immunol. 139:2551–2555, Oct. 1987.

*Primary Examiner*—Christina Y. Chan
*Assistant Examiner*—Ronald Pelley
*Attorney, Agent, or Firm*—Burns, Doane, Swecker & Mathis, L.L.P.

[57] ABSTRACT

Methods for determining the sensitizing, irritant and/or allergenic potential of a candidate substrate are provided. These methods involve simultaneously cultivating keratinocytes and Langerhans cell precursors in a nutrient medium in order to effect differentiation of the Langerhans cell precursors, and contacting the candidate substrate with the cultured cells to determine the effect if any on markers associated with sensitizing, irritant or allergenic potential.

19 Claims, No Drawings

EVALUATING THE SENSITIZING/IRRITANT/ ALLERGENIC POTENTIAL OF A GIVEN SUBSTRATE

CROSS-REFERENCE TO PRIORITY APPLICATION

This application claims priority under 35 U.S.C. §119 of FR-01576, filed Feb. 11, 1997, hereby expressly incorporated by reference.

BACKGROUND OF THE INVENTION

1. Technical Field of the Invention

The present invention relates to a procedure or technique for evaluating the sensitizing and/or irritant and/or allergenic effects of a given substrate or active agent.

2. Description of the Prior Art

The skin constitutes one most important organ of a living organism, and is acknowledged to be one of the principal active components of the immune defense system.

The natural human epidermis principally comprises three types of cells, i.e., keratinocytes, which make up the vast majority thereof, melanocytes, and Langerhans cells. By virtue of its specific functions, each of these cell types plays a role in the fundamental mechanisms of the skin of an organism. The Langerhans cells are involved in the immune-conferring defenses of the skin. It has long been known to this art that these cells serve a basic function in the host's immune defenses, in particular as the initial barrier to outside attack.

Langerhans cells are derived from the bone marrow and may be characterized by expression of the CD1a antigenic marker (CD1a-positive cells). In the epidermis, the epidermal Langerhans cells are also characterized by the presence of Birbeck granules (Rowden et al., *Nature*, 268: 247–248 (1977)). They exercise a decisive function in initiating immune responses against antigens that have invaded the skin or which the skin has newly generated. When placed in contact with an allergen, the Langerhans cells migrate to the ganglions, where they trigger specific reactions of the T cells. In this manner, they are thus comparable to the antigen-presentation cells, which are essential to the proper functioning of the T lymphocytes.

Accordingly, the main function of the Langerhans cells is to supply a sensitization signal in the skin's immune response to a wide variety of antigens, including contact allergens, tumoral antigens, and microorganisms. It may be concluded, therefore, that these cells probably play a role in a large number of skin pathologies.

Furthermore, the industry generally, and the cosmetics trade in particular, formulate new compounds into their compositions with increasing frequency. One of the major problems now confronting the industry is thus the evaluation of the adverse effects which these compounds could induce in contact with the skin, in particular as regards contact sensitization. Hence, it is essential to be able to evaluate, simply and rapidly, the sensitizing and/or irritant and/or allergenic potential of such products/compositions.

For ethical reasons, it is apparent that such evaluations cannot be carried out without problems on humans, and, preferably, they should not be conducted on animal models.

The importance and the necessity of having an in vitro model permitting a safe, rapid, reliable, and inexpensive evaluation of the risk-posing products or substrates are self-evident. Such a model would, moreover, present the additional advantage of permitting problem-free evaluation, at least in preliminary studies, of a large number of materials.

One of the principal obstacles to the development of such model resides in the fact that, in the skin, the Langerhans cells have been subjected to a specific differentiation program. WO-A-90/02796 indicates that, in a three-dimensional skin culture system, Langerhans cells isolated from fresh skin samples be added to keratinocyte and melanocyte cultures. This application also explains that it is difficult to grow these cells in culture. It emerges, in fact, that Langerhans cells purified from epidermal samples are CD1a-positive cells deriving from precursors which have matured during their differentiation cycle to the point where these cells contain Birbeck granules. Once isolated, these cells do not develop further in their differentiation cycle and no longer proliferate.

The in vitro culturing of these cells is limited to maintaining them alive, given the inability of these cells to multiply. Indeed, these cells terminate and die without having fulfilled their function. The same phenomenon is observed when the cells are added to a reconstructed skin model. Therefore, the equivalent skin thus obtained, even if it contains Langerhans cells, does not permit evaluation of the sensitizing and/or irritant and/or allergenic potential of a product, since it does not contain active Langerhans cells.

SUMMARY OF THE INVENTION

It has now surprisingly and unexpectedly been determined that differentiation of the precursors of Langerhans cells can be effected spontaneously by cultivating them in the presence of keratinocytes. Based on this phenomenon, an improved procedure for evaluating the sensitizing and/or irritant and/or allergenic potential of a substrate has been developed.

Briefly, the present invention features a procedure for evaluation of the sensitizing and/or irritant and/or allergenic potential of a product, this procedure comprising simultaneously cultivating at least the keratinocytes and Langerhans cell precursors for a period of time sufficient to cause differentiation of the Langerhans cells, next contacting the culture and the substrate to be tested for a sufficient period of time, then measuring the variation of a marker of the sensitizing and/or irritant and/or allergenic potential of said product, and thence evaluating the results of such measurement in comparison with a control.

DETAILED DESCRIPTION OF BEST MODE AND SPECIFIC/PREFERRED EMBODIMENTS OF THE INVENTION

More particularly according to the present invention, the keratinocytes employed may be prepared via any method known to this art. Exemplary are cultures of separated epidermis taken from a normal or pathological skin sample, or cultures of keratinocytes taken from normal or pathological hair follicle sheaths.

Preferably in accordance with this invention, the keratinocytes used are prepared from separated epidermis taken from a normal or pathological skin sample, using the technique described in Regnier et al., *Frontier of Matrix Biology*, Vol. 9, 4–35 (Karger, Basel 1981).

Advantageously, the keratinocytes employed per this invention are human keratinocytes.

The Langerhans cell precursors may be any cell strain capable of undergoing differentiation under the effect of induction to produce Langerhans cells; namely, capable of undergoing differentiation to produce CD1a-positive cells. Advantageously, these precursors may be CD34 hematopoietic cells (Caux et al., *Nature*, Vol. 360, November 1992, 258).

The Langerhans cell precursors may be purified from tissue in which they occur naturally, e.g., from bone marrow, peripheral blood, and umbilical cord blood.

Preferably, Langerhans cell precursors are employed from peripheral blood or umbilical cord blood, and more preferably precursors prepared from umbilical cord blood.

The Langerhans cell precursors employed in the present invention are advantageously human in origin.

Any purification technique may be employed for this purpose. Exemplary is the technique described in Caux et al., *Nature,* Vol. 360, November 1992, 258.

According to this invention, the ratio between the number of keratinocytes and the Langerhans cell precursors advantageously ranges from 95:5 to 25:75 of the percentage of the total number of cells in the culture, preferably from 75:25 to 35:65, and, even more preferably, this ratio is about 50:50.

The nutritive medium used in the procedure according to the invention may be any nutritive medium per se known for its ability to permit keratinocyte proliferation and differentiation. Exemplary is the modified Eagle-Dulbecco medium, or a specific medium containing a variable proportion of calcium, such as that described by S. T. Boyce and R. G. Ham (*J. Tissue Cult. Meth.,* 9, 83–93 (1985)). According to the invention, it is possible to use a mixture of several nutritive mediums, for example the modified Eagle-Dulbecco medium/Ham F12 or Rheinwald-Green medium (*Cell.,* 6, 331–334 (1975)).

Also according to this invention, keratinocytes and Langerhans cell precursors at the least are cultivated simultaneously for a period of time sufficient to effect differentiation of the Langerhans cell precursors. As described above, mature Langerhans cells are characterized by the presence of Birbeck granules and the expression of the CD1a antigenic marker. Thus, a sufficient culturing time is generally the minimum time required for the appearance of these characteristics. Accordingly, to provide an order of magnitude, keratinocytes and Langerhans cell precursors are cultivated simultaneously for from 1 to 30 days, preferably for a period of time of from 2 to 13 days.

Any technique for contacting the cells and entity to be tested can be used in accordance with the invention. Preferably, however, the product to be tested is placed in solution in the culture medium.

The product or substrate to be tested may exist in any form suitable for placing it in contact with the cells. In particular, it may exist in its pure molecular state or as a composition.

In general, the incubation time of the product to be tested in combination with the cell culture is determined by the time required for said culture to respond to the product with which it has been contacted, namely, the time required to elicit a modification of the level of expression of the marker of the sensitizing and/or irritant and/or allergenic potential of said product.

This incubation time may range from several seconds to several days. The incubation time normally ranges from 5 seconds to 72 hours, and preferably from 1 to 24 hours.

By the term "marker of the sensitizing and/or irritant and/or allergenic potential of said product" is intended any element whose presence, absence, modified expression, or modified distribution may be measured in response to placing the cell culture in contact with said product to be tested. Exemplary markers include a nucleic acid, a protein, a linked or unlinked protein group, an ion, a cellular organelle, a lipid, or a polyoside.

Preferably, this marker is an element which represents the reaction of the Langerhans cells to the product submitted for testing. In this regard, the book *The Immune Functions of Epidermal Langerhans Cells* (Heidrun Moll, 1995, Springer-Verlag and R. G. Landes Company, Editors) provides all of the information required for proper understanding of the immune phenomena involving Langerhans cells.

Thus, it is known that, in response to contacting with a product exhibiting a sensitizing and/or irritant and/or allergenic potential, the molecular density of the class II major histocompatibility complex (MHC) or the expression of cytokines, such as interleukin $\alpha$, interleukin-1$\beta$, the Granulocyte/Macrophage Colony Stimulating Factor (GM-CSF), the Tumor Necrosis Factor (TNF $\alpha$), the Interferon-Induced Protein 10 (IP10), the Macrophage Inflammatory Protein 2 (MIP2), or interferon $\gamma$ (IFN $\gamma$) are modified. For example, short exposure to an allergen causes an increased rate of expression of the messenger ribonucleic acids (mRNA) of IL-1$\beta$, TNF$\alpha$, IFN $\gamma$, IP 10, MIP 2, or IL $\alpha$. Preferably according to the invention, the marker of the sensitizing and/or irritant and/or allergenic potential of the product to be tested is interleukin 1-$\beta$, and, more preferably, the rate of expression of the mRNA of interleukin $\beta$.

Accordingly, the activity of the substance to be tested is thus shown by the variation of the marker selected for quantitative analysis. By the term "variation" is intended any modification of the quantity, the concentration, and the distribution of the marker analyzed.

To this end, the technique according to the invention entails a step involving quantitative analysis of the marker of the sensitizing and/or irritant and/or allergenic potential of the substrate to be tested.

After incubation, this analysis may be carried out directly on the culture medium to quantify the elements excreted by the culture, or in the cells to quantify the non-excreted elements.

Thus, and more especially in the event that the element sought is not excreted, an additional step may be considered prior to the quantitative analysis, during which the cells are ground, so as to render more accessible the marker of the activity of the tested substance submitted for analysis.

Quite obviously, whatever the technique used for implementing the procedure according to the invention, any analytic technique known to those skilled in the art may be employed. For instance, exemplary are the techniques for protein or nucleic acid analysis by colorimetry, by electrophoresis, by reverse transcription and expansion using the chain polymerization technique, mass spectrography, chromatography (gas or plate chromatography), immunological methods, or optical or electron microscopy used to measure the quantity of an organelle.

The result of the quantitative analysis, which provides the variation of the marker of the sensitizing and/or irritant and/or allergenic potential of the test product selected for analysis, is not directly used as is. It becomes advantageous only to the extent that it is compared with the result of the same analysis conducted under the same conditions, but in the absence of any contact between the culture and the product to be tested. Thus, the procedure according to the invention includes a step during which the results of the analysis are assessed in relation to a control. One skilled in this art may easily determine the nature of the control required for implementation of the procedure. Preferably, the control is an identical culture, but in the absence of contact with the product to be tested.

One advantage of the invention is that, in the field of immunology or allergology, it provides a predictive assay for testing a potentially sensitizing and/or irritant and/or allergenic product that is simple, fast, and effective.

It is readily apparent that the procedure according to the invention also permits evaluation of products capable of modifying, and in fact inhibiting, the sensitizing and/or irritant and/or allergenic effect of another product. When implemented specifically for this purpose, the invention technique described above includes an additional step corresponding to the application of a product that can modify, or even inhibit, the sensitizing and/or irritant and/or allergenic effect before, during, or after contact with the sensitizing and/or irritant and/or allergenic substrate.

Accordingly, the control is then a culture including the presence of the sensitizing and/or irritant and/or allergenic reference product, but in the absence of the product capable of modifying, or in fact inhibiting, the sensitizing and/or irritant and/or allergenic effect to be evaluated.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for evaluating the sensitizing and/or irritant and/or allergenic potential of a candidate substrate, comprising (a) mixing a culture comprising purified keratinocytes with a culture comprising purified Langerhans cell precursors and culturing the resultant mixture of cells in a suitable nutrient medium for such period of time as to effect differentiation of said Langerhans cell precursors, (b) next contacting said candidate substrate with said cultured cells for such incubation period of time as to modify the level of expression of a marker of the sensitizing and/or irritant and/or allergenic potentials of said candidate substrate, (c) then measuring the variation of such marker of the sensitizing and/or irritant and/or allergenic potential of said candidate substrate, and (d) evaluating the results of said measurement (c) in comparison with a predetermined control which control comprises a co-culture of keratinocytes and Langerhans cell precursors cultured under identical conditions, except said cells are not contacted with said candidate substrate; and correlating a difference in the level of expression of said marker or the sensitizing and/or irritant and/or allergenic potential of said candidate substrate to a positive determination that said candidate substrate affects sensitization, irritation and/or allergenicity.

2. The method as defined by claim 1, wherein the ratio between the number of keratinocytes and Langerhans cell precursors in said culture medium ranges from 95:5 to 25:75 of the percentage of the total number of cells therein.

3. The method as defined by claim 2, said ratio ranging from 75:25 to 35:65.

4. The method as defined by claim 3, said ratio being about 50:50.

5. The method as defined by claim 1, said keratinocytes being cultured from separated epidermis taken from a skin sample, or from hair follicle sheaths.

6. The method as defined by claim 1, said keratinocytes being from a skin sample.

7. The method as defined by claim 1, said keratinocytes comprising human keratinocytes.

8. The method as defined by claim 1, said Langerhans cell precursors comprising purified bone marrow, peripheral blood, or umbilical cord blood.

9. The method as defined by claim 1, said Langerhans cell precursors comprising $CD34^+$ hematopoietic cells.

10. The method as defined by claim 1, said Langerhans cell precursors being of human origin.

11. The method as defined by claim 1, said marker of the sensitizing and/or irritant and/or allergenic potential of said candidate substrate comprising a nucleic acid, a protein, a linked or unlinked protein group, an ion, a cellular organelle, a lipid, or a polyoside.

12. The method as defined by claim 1, said marker of the sensitizing and/or irritant and/or allergenic potential of said candidate substrate comprising a class II major histocompatibility protein complex (MHC), a cytokine, interleukin α, interleukin-1β, the Granulocyte/Macrophage Colony Stimulating Factor (GM-CSF), the Tumor Necrosis Factor (TNFα), the Interferon-Induced Protein 10 (IP10), the Macrophage Inflammatory Protein 2 (MIP2), or interferon γ (IFN γ).

13. The method as defined by claim 12, said marker of the sensitizing and/or irritant and/or allergenic potential of said candidate substrate comprising interleukin-1β.

14. The method as defined by claim 1, said marker of the sensitizing and/or irritant and/or allergenic potential of said candidate substrate comprising the rate of expression of the mRNA of interleukin-1β.

15. The method as defined by claim 1, said period of time (a) ranging from 1 to 30 days.

16. The method as defined by claim 15, said period of time (a) ranging from 2 to 13 days.

17. The method as defined by claim 15, said period of time (b) ranging from 5 seconds to 72 hours.

18. The method as defined by claim 17, said period of time (b) ranging from 1 to 24 hours.

19. A method for evaluating whether a second candidate substrate is capable of modifying or inhibiting the sensitizing and/or irritant and/or allergenic response of a first candidate substrate, comprising the method as defined in claim 1, further comprises adding said second candidate substrate to said culture medium before, during or after said contacting (b) with said first candidate substrate.

* * * * *